(12) United States Patent
Thys et al.

(10) Patent No.: US 10,857,278 B2
(45) Date of Patent: Dec. 8, 2020

(54) METHOD OF IDENTIFYING A FILTER

(71) Applicant: FRESENIUS MEDICAL CARE DEUTSCHLAND GMBH, Bad Homburg (DE)

(72) Inventors: Martin Thys, Grettstadt (DE); Joachim Noack, Bad Neustadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 121 days.

(21) Appl. No.: 15/515,306

(22) PCT Filed: Sep. 18, 2015

(86) PCT No.: PCT/EP2015/001867
§ 371 (c)(1),
(2) Date: Mar. 29, 2017

(87) PCT Pub. No.: WO2016/050339
PCT Pub. Date: Apr. 7, 2016

(65) Prior Publication Data
US 2018/0228959 A1  Aug. 16, 2018

(30) Foreign Application Priority Data
Sep. 29, 2014 (DE) .................. 10 2014 014 418

(51) Int. Cl.
*A61M 1/16* (2006.01)
*A61M 1/34* (2006.01)
(Continued)

(52) U.S. Cl.
CPC .......... *A61M 1/1615* (2014.02); *A61M 1/16* (2013.01); *A61M 1/1607* (2014.02); *A61M 1/1617* (2014.02); *A61M 1/34* (2013.01); *A61M 1/341* (2014.02); *A61M 1/3413* (2013.01); *A61M 1/3437* (2014.02); *A61M 1/3609* (2014.02); *A61M 1/3639* (2013.01); *B01D 61/24* (2013.01); *A61M 1/342* (2013.01); *A61M 1/3406* (2014.02); *A61M 2202/0413* (2013.01); *A61M 2205/276* (2013.01);
(Continued)

(58) Field of Classification Search
None
See application file for complete search history.

(56) References Cited

U.S. PATENT DOCUMENTS

| | | | | |
|---|---|---|---|---|
| 5,580,460 A | * | 12/1996 | Polaschegg | ......... A61M 1/1617 210/646 |
| 2004/0016700 A1 | * | 1/2004 | Kellam | ................... A61M 1/16 210/646 |

FOREIGN PATENT DOCUMENTS

| | | |
|---|---|---|
| DE | 19534417 | 3/1997 |
| EP | 1892000 | 2/2008 |

(Continued)

*Primary Examiner* — Krishnan S Menon
(74) *Attorney, Agent, or Firm* — Jacobson Holman PLLC

(57) ABSTRACT

A method of identifying a type of a filter, which has at least one retentate side and at least one permeate side separated from one another by at least one filter medium, includes generating a pressure in a fluid, in particular in a liquid, on the retentate side or on the permeate side via a pressure source. The method then includes switching off the pressure source, and measuring a pressure development in the fluid over time subsequent to the switching off of the pressure source.

2 Claims, 2 Drawing Sheets

(51) Int. Cl.
*A61M 1/36* (2006.01)
*B01D 61/24* (2006.01)

(52) U.S. Cl.
CPC ............ *A61M 2205/3331* (2013.01); *A61M 2205/3344* (2013.01); *A61M 2205/3355* (2013.01); *A61M 2205/3365* (2013.01); *A61M 2205/50* (2013.01); *A61M 2205/6018* (2013.01); *A61M 2230/207* (2013.01); *A61M 2230/30* (2013.01)

(56) References Cited

FOREIGN PATENT DOCUMENTS

| | | |
|---|---|---|
| FR | 2936713 | 4/2010 |
| WO | WO 03092371 | 11/2003 |

\* cited by examiner

METHOD OF IDENTIFYING A FILTER

BACKGROUND OF THE INVENTION

1. Field of the Invention

The present invention relates to a method of identifying a filter, wherein the filter has at least one retentate side and at least one permeate side which are separated from one another by at least one filter medium.

2. Description of Related Art

Filters having semi-permeable membranes are used in a number of apparatus for blood treatment. Such processes can, for example, be hemofiltration, hemodialysis, hemodiafiltration, apheresis, medication, etc.

Different types of filter are frequently used in blood treatments of the same kind.

Since the success of the treatment essentially depends on the type of filter used, it must be absolutely ensured that the correct filter is used for the respective treatment.

It is customary that the operator of a blood treatment device selects a filter and uses it for the treatment. In this respect, however, the case can occur that a wrong filter or an unsuitable filter is used due to error.

In methods known from the prior art, an error in the selection of the filter is precluded in that the treatment apparatus into which the filter is inserted determines the type of filter with reference to features outwardly present on the filter such as mechanical or optical features, whereby a treatment with an unsuitable filter can be prevented.

The detection of these outer features of a filter requires the use of at least one sensor or the like which is used especially for this filter recognition.

SUMMARY OF THE INVENTION

It is furthermore known from the prior art to determine the ultrafiltration constant of a filter with the aid of at least two pressure sensors in the hydraulic fluid circuits to which the filter is connected. A conclusion can be drawn on the type of filter or the ultrafiltration constant can be measured on the basis of the evaluation of the signals of the two pressure sensors. This evaluation of the signals of two or more than two pressure sensors in consecutive states of the method is, however, associated with the disadvantage of a comparatively high technical and time effort.

It is therefore the object of the present invention to further develop a method of the initially named kind such that it can be carried out simply and involves a small technical effort.

This object is achieved by a method having the features described herein. Provision is accordingly made that the method comprises generating a pressure in a fluid, in particular in a liquid such as in a dialysis solution on the retentate side or on the permeate side of the filter by means of a pressure source such as a pump. The method furthermore comprises switching off the pressure source and the measurement of the pressure development in the fluid over time subsequent thereto. The pressure measurement takes place only after the switching off of the pressure source or before and after the switching off of the pressure source.

The ultrafiltration coefficient and/or the flow resistance of the respective type of filter used can be determined in a comparatively simple manner by the measurement of the pressure development over time. If a filter is used which has a low flow resistance or a high ultrafiltration coefficient, the pressure drops by only a relatively small amount within a certain period of time after switching off the pressure source since a comparatively large fluid volume has already passed over the filter medium during the pressure build-up and a pressure build-up has thus likewise already taken place on this side.

If, in contrast, a filter having a high flow resistance or having a small ultrafiltration coefficient is used, a relatively small excess pressure is adopted on the other side of the filter medium during the pressure build-up by means of the pressure source since the passing over of fluid is correspondingly impeded. As a consequence, the pressure on that side on which the pressure source is connected drops by a relatively large amount after the switching off of the pressure source since a relatively large fluid quantity is displaced over the filter medium up to the complete pressure equalization.

It is thus possible to draw conclusions on the types of filter or on the ultrafiltration coefficient or on the flow resistance of the connected type of filter by the measurement of the pressure development.

The term of "measurement of the pressure development" in the fluid over time comprises both the measurement of a plurality of pressure values and the measurement of only one pressure value after the switching off of the pressure source. However, a particularly reliable statement on the type of filter is rather possible when a plurality of pressure values are taken in a time sequence after switching off the pressure source.

The method can be used with all devices on whose operation a filter is used having a filter medium, in particular having a semi-permeable membrane.

A dialyzer such as is used in a dialysis machine can be considered as the filter, for example. However, the term "filter" is not restricted to a dialyzer, but also comprises any other filters, for example those which are suitable and intended for use in a blood treatment device.

Provision is made in a further embodiment of the invention that the pressure development is only measured by a single pressure sensor. Provision is preferably made in this respect that the pressure is measured on that side of the filter on which the pressure has also been generated by the pressure source. This means that the pressure source and the pressure sensor are arranged on the same side (permeate side or retentate side) of the filter in this embodiment of the invention.

Provision can furthermore be made that the pressure source increases the pressure for so long until a specific pressure has been reached and the pressure source is then switched off. Subsequently to this, the recording of the pressure or the detection of pressure values over time can take place on the basis of which a conclusion can then be drawn on the types of filter.

Provision is made in a further embodiment of the invention that the retentate side and/or the permeate side of the filter is/are connected to one or more fluid lines, wherein one or more blocking valves are provided in these fluid lines and wherein these blocking valves are closed during the measurement of the pressure development over time in the fluid. The measurement of the pressure development over time thus preferably takes place in a closed system in which a measurement is made how the pressure changes over time on the side of the filter which is not in direct fluid communication with the pressure source, but is rather separated therefrom by means of the filter medium.

It is conceivable that the retentate side and the permeate side are each components of a dialysis circuit or blood circuit, that is of circuits which are flowed through by the dialysis solution, on the one hand, and by blood, on the other hand, in operation of the blood treatment apparatus. The named fluid lines in this case thus represent components of an extracorporeal circuit or components of a circuit for the dialysis solution.

A total of four lines are thus preferably provided, with a respective feed line and drain line being provided for the retentate side and for the permeate side of the filter. It is conceivable that the pump or pressure source is arranged in one of these lines and that all other lines are provided with at least one blocking valve, with said blocking valves being closed during the pressure measurement and with a stationary pump or a switched-off pressure source.

Provision is made in a further preferred embodiment of the invention that the filter is completely filled with fluid before the application of the pressure.

The present invention further relates to a system of identifying a filter, wherein the filter has at least one retentate side and at least one permeate side which are separated from one another by at least one filter medium. The system furthermore comprises at least one pressure source, in particular at least one pump which is configured such that a pressure can be generated in a fluid, in particular in a liquid on the retentate side or on the permeate side of the filter. At least one pressure sensor is furthermore provided which detects the pressure development in the fluid over time and at least one control unit is provided which is connected both to the pressure source and to the pressure sensor such that the measurement of the pressure development over time takes place only or also after the switching off of the pressure source.

The term "switching off the pressure source", for example, comprises the switching off of a pump or also the decoupling of the filter from another pressure source, for example by blocking a valve.

Provision is made in a further embodiment of the invention that the filter is a dialyzer and/or that the filter medium is a semi-permeable membrane.

As already stated above, a preferred embodiment of the invention comprises only a single pressure sensor being present on the basis of which or with whose measured values the type of filter can be determined. This pressure sensor is preferably located at that side of the filter on which the pressure is generated by the pressure source.

A particularly simple embodiment of the invention results when no further sensor is provided for determining the type of filter and in particular when no sensor is present for detecting mechanically or optically detectable filter features.

The control unit can be configured so that it operates the pressure source such that the pressure in the fluid is increased until a specific pressure is reached and subsequently switches off the pressure source. The measurement of the pressure over time then takes place. A conclusion can then be drawn on the type of filter or on the filter characteristic on the basis of this measurement.

Provision is made in a further embodiment of the invention that the retentate side and/or the permeate side of the filter is/are connected to one or more fluid lines, wherein one or more blocking valves are arranged in these fluid lines. In this respect, the control unit can be configured such that these blocking valves close during the measurement of the pressure development in the fluid over time. As already stated above, a system thereby results which is closed overall and in which the supply and the discharge lines of the retentate side and of the permeate side are blocked by blocking valves or by the pump or by another pressure source. A fluid movement in this closed system is only possible via and through the filter medium. This fluid movement produces the measurable pressure change.

The present invention furthermore relates to a blood treatment device, in particular to a dialysis machine, which comprises at least one system in accordance with the invention.

The pressure source or the pump and the pressure sensor of the apparatus is or are preferably a component of such a blood treatment device, with these components, that is the pressure source and pressure sensor, anyway being present at the blood treatment device in a preferred embodiment so that no separate equipment is required for carrying out the method.

It is, for example, conceivable that the pressure source is the pump which conveys blood or the dialysis solution in the operation of the blood treatment device and that the pressure sensor is an anyway present pressure sensor for measuring the pressure on the blood side or on the dialyzate side of the blood treatment device.

BRIEF DESCRIPTION OF THE DRAWINGS

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
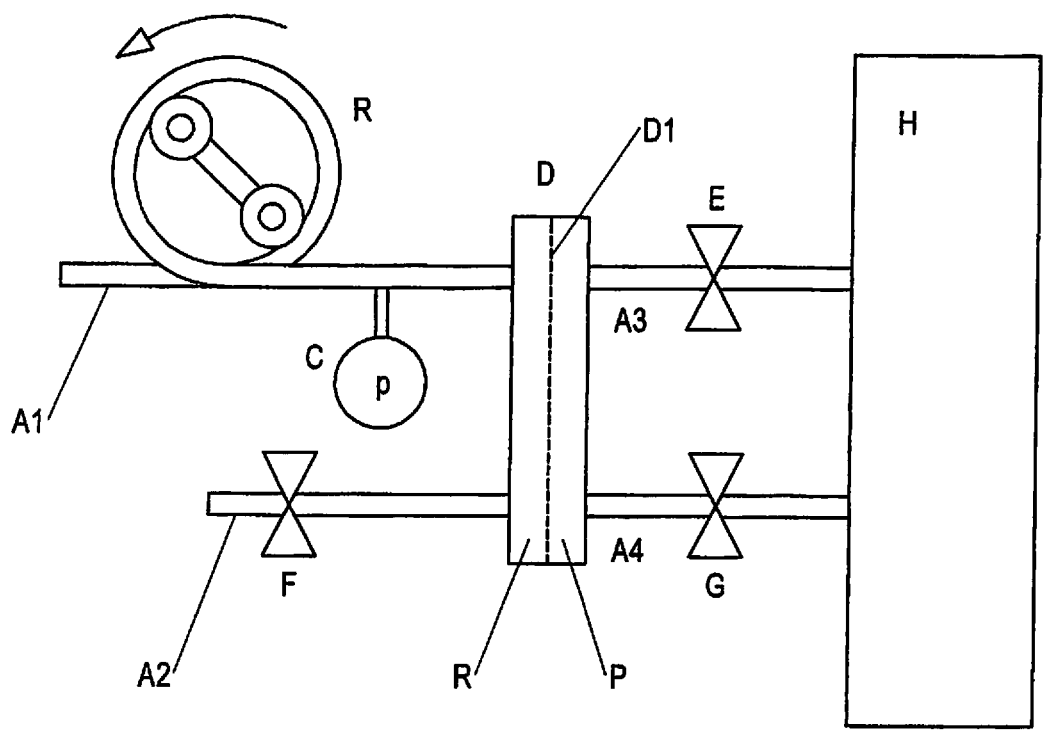
FIG. 1: a schematic view of a system in accordance with the present invention for identifying a filter.

In FIG. 1, a line or a patient connection is marked by the reference numeral A1 which is connected to the patient in the operation of a blood treatment device and, for example, conducts blood from the patient to the dialyzer D in an extracorporeal circuit.

The pump B and the dialyzer D, which is separated by a semi-permeable membrane D1 into a retentate side R and into a permeate side P, are located in this extracorporeal circuit.

The reference numeral A2 designates a second line of the extracorporeal blood circuit or a patient connection through which the retentate is conveyed back to the patient in the operation of the apparatus. As can be seen from FIG. 1, a hose clamp F, by means of which the line A2 can be blocked, is located in the line A2.

As can further be seen from FIG. 1, the permeate side P of the filter D is likewise connected to a feed line A4 and to a drain line A3. The lines A4 and A3 likewise have hose clamps G and E by means of which these lines can be blocked. Reference numeral H designates the hydraulics of the system which can, for example, be the supply of a blood treatment device with dialysis solution, pumps for conveying the dialysis solution, etc. In treatment operation, the dialysis solution is transported through the line A4 to the filter D and the dialysis solution is led off from the filter D through the line A3.

The system hoses A1 and A2 have a limited stiffness and thus represent a pressure-dependent volume.

As can furthermore be seen from FIG. 1, a pressure sensor C is located between the pump B and the filter D for measuring the pressure p.

The method of identifying the filter is designed as follows:

The pump B conveys until a specific previously selected pressure is adopted at the pressure sensor C which is arranged between the pump P and the filter D. It can in this respect, for example, be a relative pressure of 1 bar.

If this pressure is reached, this is recognized by a control unit and the pump B is switched off. A pressure is adopted by a flow over the membrane D1 in the filter D in the system hoses A3, A4 up to the time of the switching off of the pump B. This pressure is dependent on the flow resistance of the membrane D1. The smaller the flow resistance of the membrane, the more liquid flows over the membrane into the lines A3 and A4 during the operation of the pump B.

After the switching off of the pump B, a pressure equalization takes place over the membrane D1 whose speed depends on the type of filter or on the property of the filter medium. In this respect, liquid is displaced into the system hoses A3 and A4.

With a membrane having a small flow resistance or a high ultrafiltration coefficient, a relatively high excess pressure is already adopted in the hoses A3 and A4 during the operation of the pump B since a comparatively large liquid quantity already passes over the membrane D1. This has the consequence that the pressure p at the pressure sensor C only drops by a relatively small amount within a previously defined time period, for example <5 seconds, after the switching off of the pump.

Figure 2:
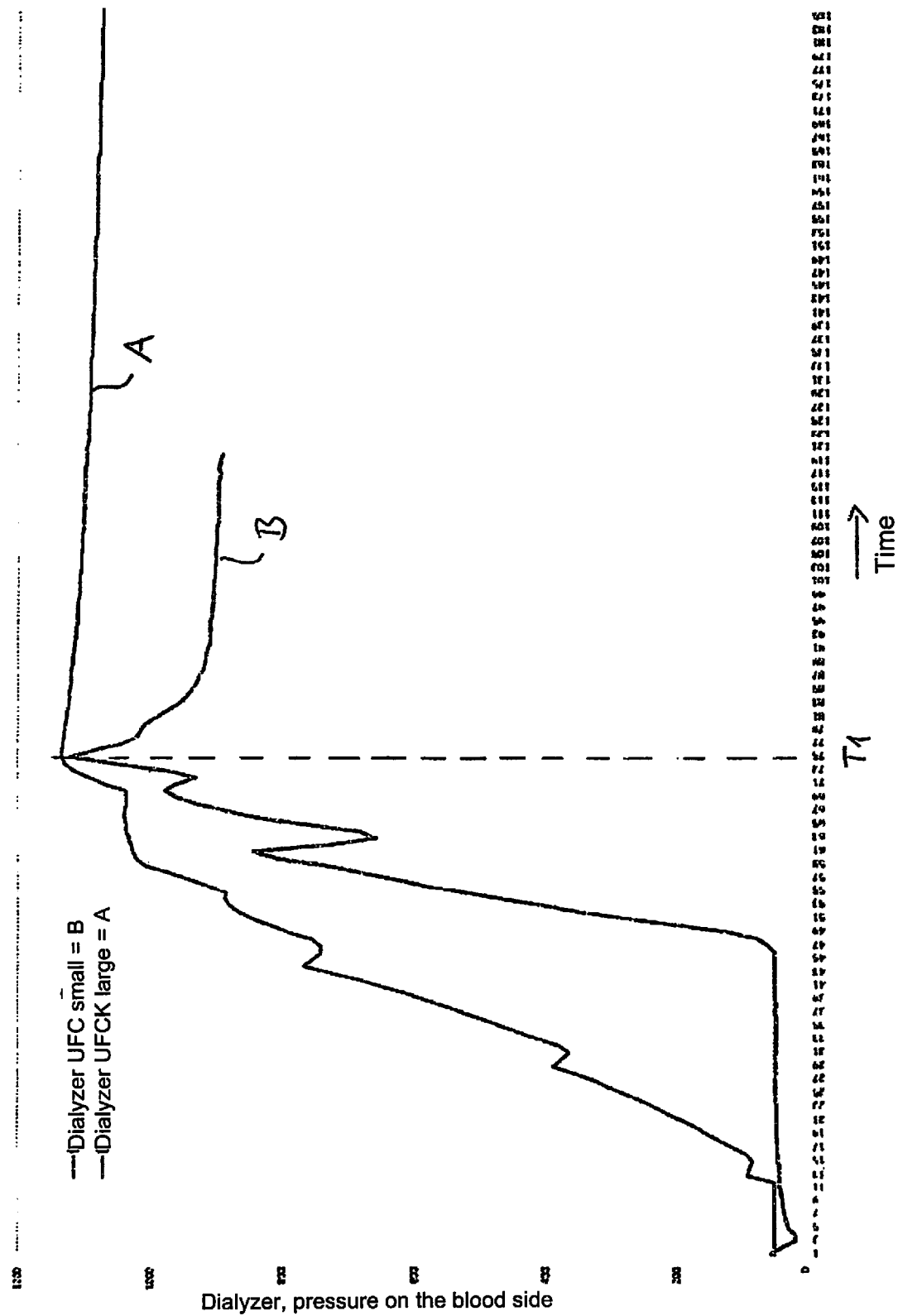
FIG. 2: time curves of the pressure on the pressure build-up and after the switching off of the pressure source for different types of filter.

This can be recognized with reference to the line A in FIG. 2. The pressure is increased by the pump up to the time T1. The pump is then switched off and the clamps E, F and G are closed. As can be seen from the pressure curve A, the pressure only drops by a relatively small amount, typically by less than 30 mm Hg, after the switching off of the pump, that is after the time T1, since only a relatively small liquid quantity is displaced over the membrane up to the complete pressure equalization.

With a membrane having a high flow resistance or a small ultrafiltration coefficient, a different pressure curve results as can be recognized with reference to the line B in FIG. 2.

With a membrane having such a high flow resistance, a relatively small excess pressure is adopted in the system hoses A3 and A4 during the conveying of the pump B since only a comparatively small amount of liquid passes over the membrane D1.

After the switching off of the pump at the time T1, the pressure p at the pressure sensor C consequently drops by a relatively high amount in the named time period, typically of 5<seconds. The pressure drop is typically above 100 mm Hg, as can be recognized from line B. This is due to the fact that a relatively large liquid amount is still displaced over the membrane up to the complete pressure equalization, which results in a corresponding pressure drop in the compartment of the filter from which the liquid is displaced.

In the embodiment, the pump B and the pressure sensor C are on the blood side. Arranging the pump and the sensor on the dialyzate side is, however, likewise covered by the invention in principle.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of determining, for a dialyzer that includes a retentate side and a permeate side which are separated from one another by a semipermeable membrane, whether the dialyzer has a high ultrafiltration coefficient or a low flow resistance, or a low ultrafiltration coefficient or a high flow resistance, said method comprising the steps of:
    connecting a pressure source pump on the retentate side inlet of the dialyzer and a pressure sensor between the dialyzer and the pump;
    providing blocking valves on the retentate side outlet, and the permeate side inlet and outlet;
    connecting a control unit to the pump, the blocking valves, and the pressure sensor;
    filling the dialyzer completely with a dialysis solution;
    closing all of the blocking valves;
    with the pump, generating a specific predetermined pressure in the dialysis solution on the retentate side;
    switching off the pump; and
    measuring a pressure drop in the dialysis fluid over time subsequent to the switching off of the pump, the pressure drop being measured by the pressure sensor,
    with the control unit being configured to measure the pressure drop over time after the switching off of the pump, and to determine the dialyzer as having the high ultrafiltration coefficient or the low flow resistance if the pressure drops by a first predefined amount within a predefined time period after the switching off of the pump, and to determine the dialyzer as having the low ultrafiltration coefficient or the high flow resistance if the pressure drops by a second predefined amount in the predefined time period after the switching off of the pump, with the second predefined amount being greater than the first predefined amount, and
    with the retentate side being the dialysate side when the permeate side is the blood side, and the retentate side being the blood side when the permeate side is the dialysate side.

2. The method in accordance with claim 1, wherein the retentate side and/or the permeate side of the dialysis filter is/are connected to one or more fluid lines, with one or more of the blocking valves being provided in the one or more fluid lines.

* * * * *